(12) United States Patent
Yokoyama et al.

(10) Patent No.: US 9,062,341 B2
(45) Date of Patent: Jun. 23, 2015

(54) SUBSTRATE USED FOR CELL MIGRATION ASSAYS AND METHOD FOR CELL MIGRATION ASSAYS

(75) Inventors: Naoki Yokoyama, Tokyo (JP); Tomonori Akai, Tokyo (JP); Yuya Takasugi, Tokyo (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 0 days.

(21) Appl. No.: 13/878,726

(22) PCT Filed: Dec. 6, 2010

(86) PCT No.: PCT/JP2010/071832
§ 371 (c)(1),
(2), (4) Date: Apr. 10, 2013

(87) PCT Pub. No.: WO2012/049784
PCT Pub. Date: Apr. 19, 2012

(65) Prior Publication Data
US 2013/0210068 A1 Aug. 15, 2013

(30) Foreign Application Priority Data

Oct. 15, 2010 (JP) ................................. 2010-232954

(51) Int. Cl.
*C12Q 1/04* (2006.01)
(52) U.S. Cl.
CPC . *C12Q 1/04* (2013.01); *C12Q 1/045* (2013.01)
(58) Field of Classification Search
IPC ........................................................ C12N 5/02
See application file for complete search history.

(56) References Cited

U.S. PATENT DOCUMENTS

2008/0113334 A1   5/2008   Hattori

FOREIGN PATENT DOCUMENTS

| JP | 6-335381 A | 12/1994 |
| JP | 2008-048684 A | 3/2008 |
| JP | 2008-118900 A | 5/2008 |

OTHER PUBLICATIONS

Liu et al. Engineered Protein and Cell Adhesivity Using PEO-Terminated Triblock Polymers; Journal of Biomedical Materials Research, vol. 60 (2002) pp. 126-134.*
Nakanishi et al. Spatiotemporal Control of Migration of Single Cells on a Photoactivatable Cell Microarray; Journal of the Americal Chemical Society, vol. 129 (2007) pp. 6694-6695.*
Fan et al. Electrically Programmable Surfaces for Configurable Patterning of Cells; Advaned Materials, vol. 20 (2008) pp. 1418-1423.*
Azioune et al. Simple and Rapid Process for Single Cell Micro-Patterning; Lab on a Chip, vol. 9 (2009) pp. 1640-1642.*
Gabia, M., et al., "Electrically controlling cell adhesion, growth and migration.", Colloids and Surfaces B: Biointerfaces, Sep. 2010, vol. 79, pp. 365-371.
Shah, S. S., et al., "Exercising spatiotemporal control of cell attachment with optically transparent microelectrodes.", Langmuir, 2008, vol. 24, No. 13, pp. 6837-6844.

* cited by examiner

*Primary Examiner* — Sharmila G. Landau
*Assistant Examiner* — Paul Martin
(74) *Attorney, Agent, or Firm* — Lucas & Mercanti, LLP

(57) ABSTRACT

This invention provides a means for cell migration assays by regulating the cells adhered to a substrate so that they migrate to a given region, which is a substrate used for cell culture comprising: a base material comprising a conductive region and an insulating region provided thereon and cell-adhesive regions and non-cell-adhesive regions provided in the conductive region and the insulating region, respectively, wherein a cell-adhesive region is positioned adjacent to a non-cell-adhesive region in the conductive region, and a cell-adhesive region is positioned adjacent to a non-cell-adhesive region in the insulating region.

10 Claims, 7 Drawing Sheets

SUBSTRATE USED FOR CELL MIGRATION ASSAYS AND METHOD FOR CELL MIGRATION ASSAYS

CROSS-REFERENCE TO RELATED APPLICATIONS

This application is a 371 of PCT/JP2010/071832, filed Dec. 6, 2010, which claims the benefit of priority from Japanese Patent Application No. 2010-232954, filed Oct. 15, 2010, the contents of each of which are incorporated herein by reference.

TECHNICAL FIELD

The present invention relates to a substrate used for cell culture and a method for cell migration assays using such substrate.

BACKGROUND ART

At present, a wide variety of animal and plant cells are cultured, and novel cell culture techniques are being developed. Cell culture techniques are conducted for the purpose of elucidation of biochemical phenomena and properties of cells, production of useful substances, and other purposes. In addition, inspection of physiological activity or toxicity of artificially synthesized drugs has been attempted with the use of cultured cells.

Some cells (many animal cells, in particular) have adhesion-dependent properties, such that they grow while adhering to other substances. Thus, such cells cannot survive for a long period of time if they are in suspension outside an organism. Culture of such adhesion-dependent cells necessitates the use of a support to which cells adhere, and a plastic culture dish that is evenly coated with a cell-adhesive protein, such as collagen or fibronectin, is generally used. Such cell-adhesive protein is known to react with cultured cells, facilitate cell adhesion, and influence cellular configurations.

Meanwhile, cell migration is associated with a variety of phases, such as immune response, embryonic morphogenesis after fertilization, and tissue repair and reproduction. Cell migration also plays a key role in progression of diseases such as cancer, atherosclerosis, and arthritis. Specifically, vascular endothelial cell migration is a critical phenomenon in pathophysiological conditions such as inflammation, atherosclerosis, and cancer metastasis. Accordingly, development of methods for cell migration assays in vitro has been attempted for a long period of time.

Examples of commercially available apparatuses used for cell migration assays include classic Boyden's chambers, cell culture inserts, FluoroBlock® (BD Biosciences), and Cell Motility HitKit® (Cellomics). With these apparatuses, however, it is difficult to control the direction of migration of adhered cells and quantitatively assay cell migration.

Non-Patent Document 1 describes a technique of controlling adhesion and non-adhesion of cells by applying an electric potential to a substrate that is not patterned and is conductive across its entire surface. However, such substrate is disadvantageous since the properties of its entire surface change upon application of an electric potential. Accordingly, such substrate cannot be used in a manner that allows cells to adhere thereto, a given region of the substrate is selectively modified to become cell adhesive, and the cells are controlled so that they migrate selectively to such cell-adhesive region.

Non-Patent Document 2 describes a method of cell culture comprising forming a non-cell-adhesive membrane on a base material comprising a conductive region and an insulating region provided thereon, applying an electric potential to a given conductive region to modify the non-cell-adhesive membrane into a cell-adhesive membrane, and allowing cells to adhere selectively to such region. In the conductive region of the substrate of Non-Patent Document 2, however, a cell-adhesive region is not adjacent to a non-cell-adhesive region. Even if cells are allowed to adhere to a region modified to become cell adhesive and another conductive region is modified to become cell adhesive with application of an electric potential, accordingly, cells that have already adhered to the substrate are unable to migrate to a non-adjacent region. Thus, assays cannot be carried out as intended.

PRIOR ART DOCUMENTS

Non-Patent Documents

Non-Patent Document 1: Jiang, X., Ferrigno, R., Mrksich, M., and Whitesides, G. M., 2003, Electrochemical desorption of self-assembled monolayers noninvasively releases patterned cells from geometrical confinements, J. Am. Chem. Soc., 125: 2366-7

Non-Patent Document 2: Sunny, S., Shah, Ji Youn Lee, Stanislav Verkhoturov, Nazgul Tuleuova, Emile A. Schweikert, Erlan Ramanculov, and Alexander Revzin, 2008, Exercising Spatiotemporal Control of Cell Attachment with Optically Transparent Microelectrodes, Langmuir 24: 6837-6844

SUMMARY OF THE INVENTION

Object to Be Attained by the Invention

It is an object of the present invention to provide a means for cell migration assays by controlling the cells adhered to the substrate so that they migrate to a specific region.

Means for Attaining the Object

The present inventors discovered that adoption of two different means for modifying a non-cell-adhesive membrane into a cell-adhesive membrane in a patterned manner would enable formation of a non-cell-adhesive region in a region adjacent to a cell-adhesive region and modification of the non-cell-adhesive region into a cell-adhesive region, thereby controlling the cells so that they migrate to specific regions. Specifically, the present invention includes the following.

(1) A substrate used for cell culture, comprising a base material comprising a conductive region and an insulating region provided thereon, cell-adhesive regions and non-cell-adhesive regions provided in the conductive region, and non-cell-adhesive regions provided in the insulating region, wherein a cell-adhesive region is positioned adjacent to a non-cell-adhesive region in the conductive region.

(2) The substrate used for cell culture according to (1), comprising a base material comprising a conductive region and an insulating region provided thereon and cell-adhesive regions and non-cell-adhesive regions provided in the conductive region and in the insulating region, respectively, wherein a cell-adhesive region is positioned adjacent to a non-cell-adhesive region in the conductive region and a cell-adhesive region is positioned adjacent to a non-cell-adhesive region in the insulating region.

(3) The substrate used for cell culture according to (1) or (2), wherein the non-cell-adhesive region in the conductive region can be modified to become cell adhesive by applying an electric potential to the conductive region.

(4) The substrate used for cell culture according to any of (1) to (3), wherein the cell-adhesive region is modified from a non-cell-adhesive hydrophilic membrane comprising an organic compound containing a carbon-oxygen bond by oxidation and/or degradation and the non-cell-adhesive region is composed of a hydrophilic membrane comprising an organic compound containing a carbon-oxygen bond.

(5) The substrate used for cell culture according to any of (1) to (4), wherein the conductive region is patterned in a comb shape comprising a plurality of comb-tooth regions and a base supporting an individual comb-tooth region.

(6) The substrate used for cell culture according to (5), wherein the non-cell-adhesive region is patterned in an elongated region that is positioned to be orthogonal to the comb-tooth region.

(7) The substrate used for cell culture according to (5) or (6), wherein the width of the comb-tooth region in the conductive region is 0.1 μm to 500 μm.

(8) The substrate used for cell culture according to any of (5) to (7), wherein the intervals between the comb-tooth regions in the conductive region are between 10 μm and 1,000 μm.

(9) The substrate used for cell culture according to (4), wherein the organic compound containing a carbon-oxygen bond is an alkylene glycol oligomer.

(10) The substrate used for cell culture according to any of (1) to (9), wherein the conductive region comprises an indium tin oxide membrane on the surface of the base material.

(11) A method for cell migration assays comprising:
(i) a step of seeding cells on the substrate used for cell culture according to any of (1) to (10) to allow the cells to adhere to the cell-adhesive region;
(ii) a step of applying an electric potential to the conductive region so as to modify a non-cell-adhesive region in the conductive region into a cell-adhesive region; and
(iii) a step of observing the cells adhered to the cell-adhesive region in the conductive region that migrate to the region modified to become cell adhesive in step (ii).

(12) A method for producing a substrate used for cell culture comprising:
a step of forming a non-cell-adhesive hydrophilic membrane comprising an organic compound containing a carbon-oxygen bond across the entire surface of the base material comprising a conductive region and an insulating region; and
a step of modifying a hydrophilic membrane to become cell adhesive by oxidation and/or degradation in a patterned manner, so as to position a cell-adhesive region adjacent to a non-cell-adhesive region in the conductive region.

(13) The substrate used for cell culture according to any of (1) to (10),
wherein the conductive region comprises a line-shaped conductive region,
insulating regions are provided on both sides of the line-shaped conductive region along the longitudinal direction,
the line-shaped conductive region comprises one or more cell-adhesive regions entirely or partially composed of the line-shaped conductive region(s) provided at one position or at two or more positions different along the longitudinal direction,
when the line-shaped conductive region is part of the cell-adhesive region, the cell-adhesive region further includes an insulating region adjacent thereto, the line-shaped conductive region and regions outside the cell-adhesive region in insulating regions provided on both sides of the line-shaped conductive region along the longitudinal direction are non-cell-adhesive regions, and
when the dimension in the longitudinal direction of the line-shaped conductive region of a cell-adhesive region is defined as the length of the cell-adhesive region and the dimension in the direction orthogonal to the longitudinal direction is defined as the width of the cell-adhesive region, the length and the width of each cell-adhesive region are 1 μm to 500 μm, the line width of a region outside the cell-adhesive region in the line-shaped conductive region is 0.1 μm to 10 μm, and the line width is smaller than the width of the cell-adhesive region adjacent thereto.

(14) The substrate used for cell culture according to (13), wherein the non-cell-adhesive region in the conductive region can be modified to become cell adhesive by application of an electric potential to the conductive region.

(15) The substrate used for cell culture according to (14), wherein the cell-adhesive regions are provided at two or more positions different along the longitudinal direction of the line-shaped conductive region.

(16) A method for cell assays comprising:
(i) a step of seeding cells on the substrate used for cell culture according to (14) to allow the cells to adhere to the cell-adhesive region;
(ii) a step of applying an electric potential to the line-shaped conductive region so as to modify a non-cell-adhesive region in the line-shaped conductive region into a cell-adhesive region; and
(iii) a step of observing cells adhered to the cell-adhesive region.

(17) A method for providing a circuit-like cellular construct comprising:
(i) a step of seeding cells on the substrate used for cell culture according to (15) to allow the cells to adhere to the cell-adhesive region;
(ii) a step of applying an electric potential to the line-shaped conductive region so as to modify a non-cell-adhesive region in the line-shaped conductive region into a cell-adhesive region; and
(iii) a step of performing cell culture so as to morphologically change the cells adhered to the cell-adhesive region and forming a linker section between adjacent cells through the line-shaped conductive region modified into the cell-adhesive region in step (ii).

(18) The method according to (16) or (17), wherein step (i) comprises allowing a single cell to adhere to a single cell-adhesive region.

This description includes part or all of the content as disclosed in the description and/or drawings of Japanese Patent Application No. 2010-232954, which is a priority document of the present application.

Effects of the Invention

According to the present invention, a system that enables assays of cells migrating while adhering to a support in a simple manner is provided, and such system can be used for screening in the field of drug discovery.

EMBODIMENTS FOR CARRYING OUT THE INVENTION

Figure 1:
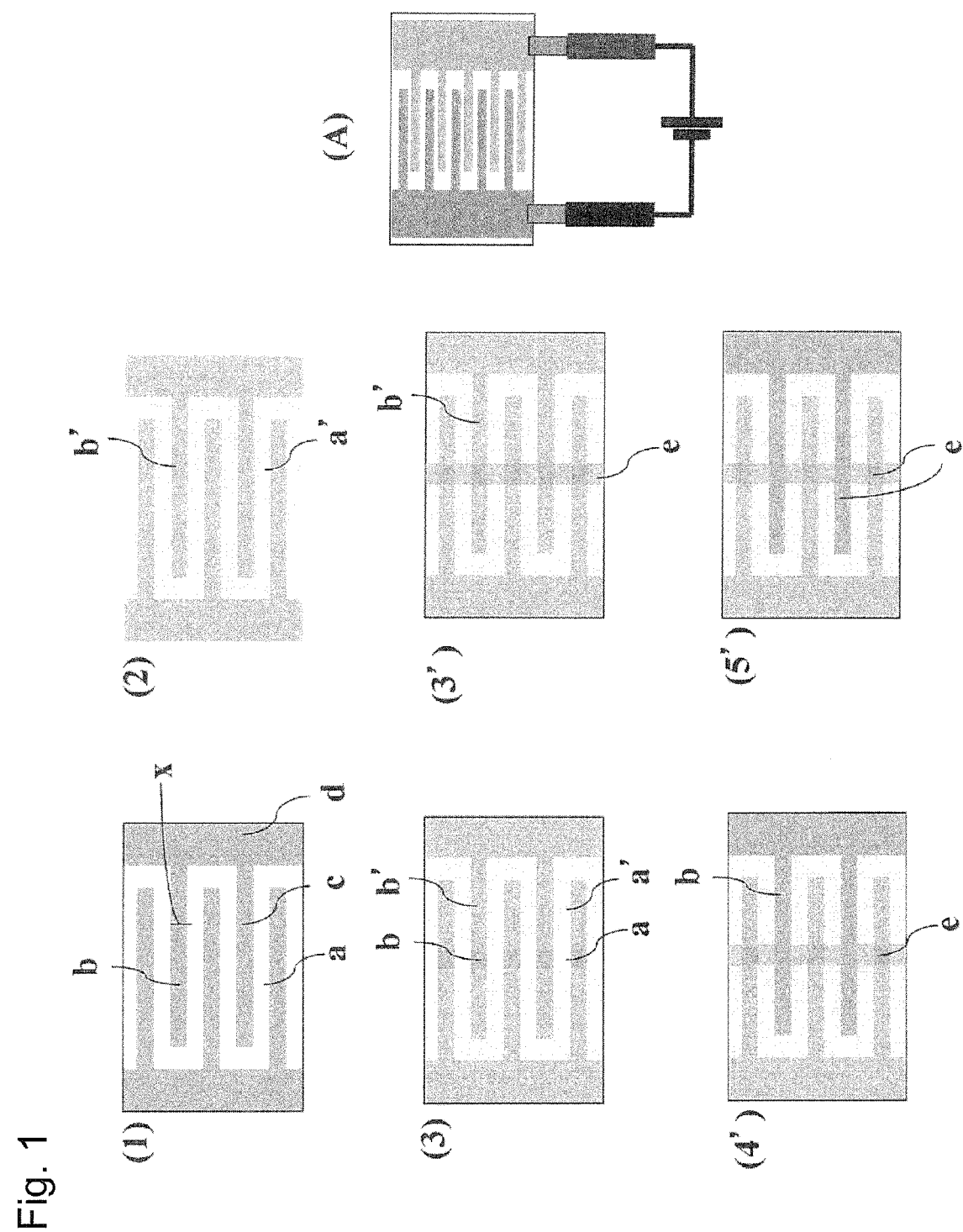
FIG. 1 shows an embodiment of the present invention.

The substrate used for cell culture of the present invention comprises: a base material comprising a conductive region (a conductive section) and an insulating region (an insulating section); cell-adhesive regions and non-cell-adhesive regions provided in the conductive region (the conductive section); and non-cell-adhesive regions provided in the insulating region (the insulating section). Such substrate is characterized in that a cell-adhesive region is positioned adjacent to a non-cell-adhesive region in a conductive region (a conductive section). The substrate used for cell culture of the present invention preferably comprises cell-adhesive regions and non-cell-adhesive regions in a patterned manner. It is occasionally preferable that cell-adhesive regions and non-cell-adhesive regions be provided in an insulating region (an insulating section) and that a cell-adhesive region be positioned adjacent to a non-cell-adhesive region in the insulating region (the insulating section).

According to the present invention, the term "cell adhesiveness" (and variations thereof) refers to a condition in which a cell adheres to a substance of interest or a cell is likely to adhere to a substance of interest. In contrast, the term "non-cell-adhesiveness" (and variations thereof) refers to a condition in which a cell is less likely to adhere to another substance or a cell does not adhere to another substance. When cells are seeded on a substrate comprising cell-adhesive regions and non-cell-adhesive regions in a patterned manner, accordingly, cells adhere to cell-adhesive regions, but cells do not adhere to non-cell-adhesive regions. Thus, cells would be aligned in a patterned manner on the surface of the substrate.

Since cell adhesiveness varies depending on types of cells to adhere thereto, the term "cell adhesiveness" refers to a condition in which a substance has adhesiveness to a given type of cell. Accordingly, a plurality of cell-adhesive regions corresponding to a plurality of types of cells may be present on a substrate used for cell culture; that is, two or more different cell-adhesive regions with different degrees of cell adhesiveness may be present.

Examples of structures of cell-adhesive regions and non-cell-adhesive regions of the substrate used for cell culture of the present invention include the two embodiments described below.

According to a first embodiment, a cell-adhesive region is prepared by subjecting a non-cell-adhesive hydrophilic membrane comprising an organic compound containing a carbon-oxygen bond to oxidation and/or degradation. According to this embodiment, a non-cell-adhesive hydrophilic membrane comprising an organic compound containing a carbon-oxygen bond is provided across the entire surface of the base material, and a region of interest is subjected to oxidation and/or degradation so as to be modified to become cell adhesive. Thus, a region of interest can be modified into a cell-adhesive region. A region that is not subjected to the treatment described above is a non-cell-adhesive region.

According to a second embodiment, a cell-adhesive region is composed of a hydrophilic membrane comprising an organic compound containing a carbon-oxygen bond at low density. While a hydrophilic membrane comprising an organic compound containing a carbon-oxygen bond at high density has non-cell-adhesiveness, a hydrophilic membrane comprising such composition at low density has cell adhesiveness. This embodiment is based on such features. A first region to which such compound is likely to bind and a second region to which such compound is less likely to bind are provided on the surface of the base material, and a membrane of such composition is provided on the surface of the base material. Thus, the first region is converted into a non-cell-adhesive region, and the second region is converted into a cell-adhesive region.

Further, a non-cell-adhesive region in the conductive region of the substrate used for cell culture of the present invention can be modified into a cell-adhesive region by application of an electric potential, and preferably a positive electric potential, to the conductive region. A region modified to become cell adhesive by application of an electric potential occasionally has surface properties that are different from those of a cell-adhesive region prepared by subjecting a non-cell-adhesive hydrophilic membrane comprising an organic compound containing a carbon-oxygen bond to oxidation and/or degradation as described above.

(Base Material)

A base material used for the substrate used for cell culture of the present invention is not particularly limited, provided that the substrate is made of a material capable of comprising a conductive region and an insulating region provided thereon. It is preferable that a conductive region and an insulating region be provided by providing a conductive region on a base material comprising an insulating material. A base material is preferably composed of a material that can comprise a membrane of an organic compound containing a carbon-oxygen bond provided on its surface. Specific examples include organic materials represented by glass, silica glass, borosilicate glass, alumina, sapphire, ceramics, forsterite, photosensitive glass, ceramic, silicon, elastomer, and plastics (e.g., polyester resin, polyethylene resin, polypropylene resin, ABS resin, nylon, acrylic resin, fluorocarbon resin, polycarbonate resin, polyurethane resin, methylpentene resin, phenolic resin, melamine resin, epoxy resin, and vinyl chloride resin). The configuration thereof is not limited, and examples include: two-dimensional configurations, such as flat plates, flat membranes, films, and porous membranes; three-dimensional configurations, such as cylinders, stamps, multi-well plates, and microchannels; and configurations having concave-convex patterns on the surfaces. When a film is used, the thickness thereof is not particularly limited, and it is generally 0.1 μm to 1,000 μm, preferably 1 μm to 500 μm, and more preferably 10 μm to 200 μm.

When a base material having a fine concave-convex pattern of about 1 nm to 10 μm that is smaller than the size of a cell provided on its surface is used and cell-adhesive regions in a conductive region and an insulating region have similar configurations, in particular, the configurations and behavior of the adhered cells may be controlled so as to effectively conduct assays. The term "fine concave-convex" refers to, for example, a depth of 1 nm to 10 μm, a convex line width of 1 nm to 10 μm, and a concave line width of 1 nm to 10 μm, in the case of line patterns.

When a conductive region is provided on a base material comprising an insulating material, a conventional patterning technique can be employed. Examples of conventional patterning techniques include various printing techniques, such as gravure printing, screen printing, offset printing, flexography, and contact printing, various lithography techniques, inkjet methods, and three-dimensional shaping, such as carving of fine grooves. Specifically, a conductive material, such as a metal or metal oxide membrane, is provided on a base material comprising an insulating material, such as a glass base material, and the resulting membrane is subjected to a conventional patterning technique, such as photolithography. Thus, a conductive region and an insulating region can be provided.

A conductive membrane can be provided on a base material using a conventional technique. Examples thereof include microwave plasma chemical vapor deposition (CVD), electric cyclotron resonance chemical vapor deposition (ECRCVD), inductive coupled plasma (ICP), DC sputtering, electric cyclotron resonance (ECR), sputtering, ionized vapor deposition, arc vapor deposition, laser vapor deposition, electron beam (EB) vapor deposition, and resistance heating vapor deposition techniques. A membrane may be provided by coating. Spin coating and various printing techniques can also be employed.

Examples of conductive membranes constituting a conductive region include a metal membrane or a metal oxide membrane, a membrane comprising metal fine particles or metal nanofibers dispersed in an insulator, and a membrane comprising a conductive organic material. Examples of metal oxides include indium tin oxide (ITO) and indium zinc oxide (IZO). Examples of metal fine particles include silver, gold, and copper fine particles. An example of metal nanofibers is carbon nanotubes. An example of a conductive organic material is polyethylenedioxythiophene (PEDOT).

A conductive membrane is not particularly limited, and a transparent membrane is preferable. Examples thereof include an ITO membrane, an IZO membrane, and a conductive polymeric membrane, such as a polyethylenedioxythiophene membrane. A membrane preferably remains transparent after an electric potential is applied. In the present invention, it is preferable that a conductive region be provided by forming an ITO membrane by sputtering, followed by patterning. A transparent membrane is advantageous in terms of cell observation.

The thickness of a conductive membrane is generally from that of a monomolecular membrane to approximately 100 μm, preferably 2 nm to 1 μm, and more preferably 5 nm to 500 nm.

A conductive region is preferably patterned in a comb shape comprising a plurality of comb-tooth regions and a base supporting an individual comb-tooth region. In such a case, the width of a comb-tooth region in the conductive region (the width on the side orthogonal to the direction of a comb-tooth region spreading from the base; i.e., the longitudinal direction of the comb-tooth region, indicated by "x" in FIG. 1 (1)) is preferably 0.1 μm to 500 μm. For the purpose of observation of cell migration, such width is preferably 5 μm to 500 μm, and more preferably 10 μm to 200 μm. If the width of a comb-tooth region is excessively small, the electric resistance in the longitudinal direction is elevated in the comb-tooth region, and the electric potential in the longitudinal direction of the comb-tooth region is likely to fall when an electric potential of a given level is applied. This makes it difficult to control electric potentials. Since the degree of lowering in an electric potential level varies depending on the conductivity of a conductive material used, the minimum width of a comb-tooth region is adequately determined in accordance with the conductivity of a conductive material, and it is preferably at least 5 μm, in general. When the width of a conductive region on a base material falls below 5 μm, a broad electrode is provided on the base material, part of the electrode surface is covered by an insulating membrane, and a region of a desirable width that is less than 5 μm is selectively exposed to convert such region into a conductive region. Thus, the problem of high resistivity causing lowering of the electric potential level can be resolved. When the width of a comb-tooth region is smaller than the size of a cell to be assayed, it is difficult for a cell to adhere to the comb-tooth region. When cell migration is observed, accordingly, the width of a comb-tooth region is adequately determined in accordance with a size of a cell to be assayed, and it is preferably at least 10 μm, in general. When the width of a comb-tooth region is large, the number of comb teeth entering the field of vision at the time of microscopic observation is reduced, and this is disadvantageous in terms of statistical processing. In general, the microscopic field of view is several mm or smaller. Accordingly, the width of a comb-tooth region is preferably 500 μm or less in order to allow at least 1 comb-tooth region to enter in the field of view. If the width of a comb-tooth region is excessively small, the migration direction of a cell to be assayed is restricted, and this results in an extended migration distance with the elapse of a given period of time. This may be advantageous for assays. The intervals between comb-tooth regions are preferably 10 to 1,000 μm, and more preferably 50 to 500 μm. If the interval between comb-tooth regions is too small, cells cross over a non-cell-adhesive region in an insulating region between comb-tooth regions, and cells are likely to migrate between adjacent comb-tooth regions. This makes it difficult to control the direction of cell migration. Accordingly, in general, the interval between comb-tooth regions is preferably at least 10 μm, and more preferably at least 50 μm. When the interval between comb-tooth regions is excessively large, the number of comb teeth entering the field of vision at the time of microscopic observation is reduced, and this is disadvantageous in terms of statistical processing. In general, the microscopic field of view is several mm or smaller. Accordingly, the width of the comb-tooth regions is preferably 1,000 μm or less. Two comb-shaped patterns in which a comb-tooth region is engaged with another comb-tooth region are particularly preferable. Such patterns are preferable since the current effectively flows when an electric potential is applied at the time of cell migration assays.

Specifically, patterning of the conductive region as described above can be performed by subjecting the prepared metal membrane or metal oxide membrane to resist coating, exposure using a photomask, development, and etching.

(Non-Cell-Adhesive Region)

It is preferable that a non-cell-adhesive region be composed of a hydrophilic membrane comprising an organic compound containing a carbon-oxygen bond. Such hydrophilic membrane is a thin membrane made mainly from a water-soluble or water-swelling organic compound containing a carbon-oxygen bond, and any membrane can be used without particular limitation, provided that it has non-cell-adhesiveness before oxidation and has cell adhesiveness after oxidation and/or degradation.

In the present invention, the term "carbon-oxygen bond" refers to a bond between carbon and oxygen, and it may be a single or double bond. Examples of carbon-oxygen bonds include C—O, C(=O)—O, and C=O.

Examples of main components include a water-soluble polymer, a water-soluble oligomer, a water-soluble organic compound, a surfactant, and an amphiphilic agent. These substances physically or chemically crosslink to each other, the resultant physically or chemically binds to a base material, and a hydrophilic thin membrane can then be obtained.

Specific examples of water-soluble polymeric materials include polyalkylene glycol and a derivative thereof, polyacrylic acid and a derivative thereof, polymethacrylic acid and a derivative thereof, polyacrylamide and a derivative thereof, polyvinyl alcohol and a derivative thereof, a zwitterionic polymer, and a polysaccharide. A molecular configuration can be, for example, line-shaped, branched, or dendrimeric. More specific examples include, but are not limited to, polyethylene glycol, a copolymer of polyethylene glycol and polypropylene glycol, such as Pluronic F108 and Pluronic F127, poly(N-isopropylacrylamide), poly(N-vinyl-2-pyrollidone), poly(2-hydroxyethyl methacrylate), poly(methacryloyloxyethyl phosphorylcholine), a copolymer of methacryloyloxyethyl phosphorylcholine and acrylic monomer, dextran, and heparin.

Specific examples of water-soluble oligomeric materials and water-soluble low-molecular-weight compounds include an alkylene glycol oligomer and a derivative thereof, an acrylate oligomer and a derivative thereof, a methacrylate oligomer and a derivative thereof, an acrylamide oligomer and a derivative thereof, a saponification product of a vinyl acetate oligomer and a derivative thereof, an oligomer comprising zwitterionic monomers and a derivative thereof, an acrylic acid and a derivative thereof, a methacrylic acid and a derivative thereof, an acrylamide and a derivative thereof, a zwitterionic compound, a water-soluble silane coupling agent, and a water-soluble thiol compound. More specific examples include, but are not limited to, an ethylene glycol oligomer, an (N-isopropylacrylamide) oligomer, a methacryloyloxyethyl phosphorylcholine oligomer, low-molecular-weight dextran, low-molecular-weight heparin, oligoethylene glycol thiol, ethylene glycol, diethylene glycol, triethylene glycol, tetraethylene glycol, 2-[methoxy(polyethyleneoxy)-propyltrimethoxysilane], and triethylene glycol-terminated-thiol.

It is preferable that a hydrophilic membrane have strong non-cell-adhesiveness before treatment and exhibit cell adhesiveness after oxidation and/or degradation.

The average hydrophilic membrane thickness is preferably 0.8 nm to 500 μm, more preferably 0.8 nm to 100 μm, further preferably 1 nm to 10 μm, and most preferably 1.5 nm to 1 μm. An average thickness of at least 0.8 nm is preferable since protein adsorption and cell adhesion are less likely to be influenced by a region that is not covered by a hydrophilic thin membrane on the surface of a substrate. If the average thickness is 500 μm or less, coating can be performed in a relatively simple manner.

A hydrophilic membrane can be provided on the surface of a base material by, for example, a method in which a hydrophilic organic compound is directly adsorbed to a base material, a method in which a base material is directly coated with a hydrophilic organic compound, a method in which a base material is directly coated with a hydrophilic organic compound, followed by crosslinking, a method in which a hydrophilic thin membrane is formed in multiple steps in order to improve adhesion to the base material, a method in which an undercoat layer is provided on a substrate in order to improve adhesion to a substrate and a hydrophilic organic compound is then applied thereon, and a method in which an origin of polymerization is provided on the surface of the substrate and a hydrophilic polymer brush is then polymerized thereon.

Among the methods described above, the method in which a hydrophilic thin membrane is formed in multiple steps and the method in which an undercoat layer is provided on a base material in order to improve adhesion of a hydrophilic organic compound to the base material and a hydrophilic organic compound is then applied thereon are particularly preferable because adhesion of the hydrophilic organic compound to the base material can be easily improved by such methods. In the description of the present invention, the term "binding layer" is used. The term "binding layer" refers to a layer that is located between the outermost hydrophilic thin membrane and a substrate, when a thin membrane of a hydrophilic organic compound is formed in multiple steps. When an undercoat layer is provided on the surface of the base material and a hydrophilic thin membrane is provided thereon, the term refers to the undercoat layer. The binding layer preferably comprises a material having a binding section (i.e., a linker). Examples of combinations of a linker and a terminal functional group of a material to be bound to the linker include an epoxy group and a hydroxyl group, phthalic anhydride and a hydroxyl group, a carboxyl group and N-hydroxysuccinimide, a carboxyl group and carbodiimide, and an amino group and glutaraldehyde. Either substance in such a combination may serve as a linker. According to such methods, a binding layer is provided by a linker-containing material on the substrate before coating the substrate with a hydrophilic material. The density of the material in the binding layer is an important factor that defines the binding force. Such density can be easily evaluated using the water contact angle on the surface of a binding layer as an indicator. In the case of a silane coupling agent having an epoxy group at its terminus (i.e., epoxysilane), for example, the water contact angle on the surface of the substrate to which epoxysilane has been added is typically at least 45 degrees, and preferably at least 47 degrees. If such conditions are satisfied, an ethylene glycol-based material or the like may then be added in the presence of an acid catalyst. Thus, a substrate with sufficient non-cell-adhesiveness can be prepared.

The term "water contact angle" used in the present invention refers to a water contact angle that is measured at 23° C.

(Formation of Cell-Adhesive Region by Oxidation and/or Degradation of Hydrophilic Membrane)

According to the present invention, a cell-adhesive region is prepared by subjecting a non-cell-adhesive hydrophilic membrane comprising an organic compound containing a carbon-oxygen bond to oxidation and/or degradation.

In the present invention, the term "oxidation" is used in a limited sense, and it refers to a reaction by which an organic compound reacts with oxygen and oxygen content is increased thereby.

The term "degradation" used herein refers to a change in which a bond of an organic compound is cleaved and two or more types of organic compounds are generated from a single type of organic compound. Typical examples of "degradation" include, but are not limited to, degradation by oxidation and degradation by ultraviolet application. When "degradation" involves oxidation (i.e., oxidative degradation), the term "degradation" and the term "oxidation" refer to the same procedure.

Through degradation by ultraviolet application, an organic compound absorbs ultraviolet rays and degrades through the excited state. When ultraviolet rays are applied to a system in which an organic compound and a molecular species containing oxygen (e.g., oxygen or water) are present, degradation takes place upon ultraviolet absorption by the compound. In addition, such molecular species is occasionally activated and allowed to react with an organic compound. The latter reaction can be classified as "oxidation." The reaction in which an organic compound degrades by oxidation caused by an activated molecular species can be classified as "degradation by oxidation" instead of "degradation by ultraviolet application."

As described above, the "oxidation" procedure occasionally overlaps with the "degradation" procedure, and such procedures cannot be clearly distinguished from each other. Accordingly, the term "oxidation and/or degradation" is used herein.

Examples of oxidation and/or degradation techniques include a method in which a hydrophilic membrane is irradiated with ultraviolet rays, a method in which a hydrophilic membrane is treated with a photocatalyst, and a method in which a hydrophilic membrane is treated with an oxidizing agent. According to the present invention, cell-adhesive regions and non-cell-adhesive regions are provided in a conductive region, and preferably in an insulating region. Thus, a hydrophilic membrane is partially subjected to oxidation and/or degradation in a patterned manner. Partial oxidation and/or degradation can be carried out with the use of masks such as photomasks or stencil masks or stamps. Alternatively, oxidation and/or degradation can be carried out by direct imaging using a laser, such as an ultraviolet laser.

Ultraviolet application is preferably carried out using, as a light source, a lamp that emits ultraviolet rays in the VUV to UV-C spectral regions, such as a mercury lamp that emits ultraviolet rays at a wavelength of 185 nm or 254 nm or an excimer lamp that emits ultraviolet rays at a wavelength of 172 nm. Photocatalytic treatment is preferably carried out using a light source that emits ultraviolet rays at a wavelength of 365 nm or lower, and use of a light source that emits ultraviolet rays at a wavelength of 254 nm or lower is more preferable. Titanium oxide or titanium oxide activated by a metal ion or metal colloid is preferably used as a photocatalyst. An organic acid or inorganic acid can be used as an oxidizing agent without particular limitation; however, it is difficult to handle highly concentrated acid. Thus, acid concentration is preferably reduced to 10% or lower. The optimal durations of ultraviolet application, treatment with a photocatalyst, and treatment with an oxidizing agent can be adequately determined in accordance with conditions such as the ultraviolet intensity of a light source to be used, activity of a photocatalyst, and oxidative power and concentration of an oxidizing agent.

A cell-adhesive region may be composed of a hydrophilic membrane comprising an organic compound containing a carbon-oxygen bond at low density. According to the present embodiment, a cell-adhesive region and a non-cell-adhesive region are each composed of a hydrophilic membrane comprising an organic compound containing a carbon-oxygen bond. Density of the organic compound in one region differs from that in another region. As the density of the organic compound is elevated, cell adhesion is less likely to occur. In a cell-adhesive region, the density of the organic compound is low enough for cell adhesion to take place. On the other hand, the density of the organic compound is excessively high in a non-cell-adhesive region, and thus cell adhesion does not take place.

An example of a method for regulating the density of a hydrophilic organic compound is a method in which a binding layer is provided between a thin membrane of a hydrophilic organic compound and the surface of a base material, so as to regulate the force with which the binding layer binds to a hydrophilic organic compound. The "binding layer" is as defined above, and it can be composed of a preferable material described above. The force of the binding layer is increased as the density of a linker-containing material in the binding layer is increased, and the force is decreased as such density is decreased. The density of a linker-containing material in the binding layer can be easily evaluated using the water contact angle on the surface of a binding layer as an indicator, as described above.

According to this embodiment of the present invention, the density of a linker-containing material is low in the binding layer in the cell-adhesive region. The water contact angle on the surface of the binding layer before a thin membrane of a hydrophilic organic compound is provided in a cell-adhesive region is typically 10 degrees to 43 degrees, and preferably 15 degrees to 40 degrees when, for example, a silane coupling agent having an epoxy group at its terminus is used as a linker-containing material. Such binding layer can be formed by providing a coating of a linker-containing material (i.e., a binding layer) on the surface of a base material and subjecting the surface of the binding layer to oxidation and/or degradation. Examples of methods of subjecting the surface of the binding layer to oxidation and/or degradation include a method in which the surface is irradiated with ultraviolet rays, a method in which the surface is treated with a photocatalyst, and a method in which the surface is treated with an oxidizing agent. The surface of the binding layer may be partially or entirely subjected to oxidation and/or degradation. Partial oxidation and/or degradation can be carried out with the use of masks such as photomasks or stencil masks or stamps. Alternatively, oxidation and/or degradation can be carried out by direct imaging using a laser, such as a ultraviolet laser. The same conditions employed for formation of a cell-adhesive region by oxidation and/or degradation of a hydrophilic membrane can be employed herein. By providing a thin membrane of a hydrophilic organic compound on the binding layer thus formed, a cell-adhesive region can be provided.

According to this embodiment of the present invention, the density of a linker-containing material is high in the binding layer in the non-cell-adhesive region. The water contact angle on the surface of the binding layer before a thin membrane of a hydrophilic organic compound is provided in a non-cell-adhesive region is typically at least 45 degrees, and preferably at least 47 degrees when, for example, a silane coupling agent having an epoxy group at its terminus is used as a linker-containing material. Such binding layer can be formed by providing a coating of a linker-containing material on the surface of a base material. When the surface of the binding layer is partially subjected to oxidation and/or degradation, a region remaining untreated serves as a binding layer that has the water contact angle described above. By providing a thin membrane of a hydrophilic organic compound on the binding layer thus formed, a non-cell-adhesive region can be provided.

(Comparison of Cell-Adhesive Region and Non-Cell-Adhesive Region)

Carbon content in the cell-adhesive region (including the binding layer when it exists) is preferably lower than that in the non-cell-adhesive region (including the binding layer when it exists). Specifically, carbon content in the cell-adhesive region is preferably 20% to 99% of that in the non-cell-adhesive region. Carbon content within such range is particularly preferable when the hydrophilic membrane thickness is 10 μm or less (the total of the binding layer thickness and the hydrophilic membrane thickness when a binding layer exists). Carbon content (atomic concentration, %) is as defined below.

The percentage of carbon bound to oxygen in the cell-adhesive region (including the binding layer when it exists) is preferably lower than that of carbon bound to oxygen in the non-cell-adhesive region (including the binding layer when it exists). Specifically, the percentage of carbon bound to oxygen in the cell-adhesive region is preferably 35% to 99% of that of carbon bound to oxygen in the non-cell-adhesive region. A percentage within such range is particularly preferable when the hydrophilic membrane thickness is 10 μm or less (the total of the binding layer thickness and the hydrophilic membrane thickness when a binding layer exists). The percentage of carbon bound to oxygen (atomic concentration, %) is as defined below.

(Method for Evaluation of Hydrophilic Thin Membrane)

The hydrophilic thin membrane of the present invention (including the binding layer when it exists) can be evaluated by contact angle measurements, ellipsometry, atomic force microscope observation, electron microscope observation, Auger electron spectroscopy, X-ray photoelectron spectroscopy, various mass spectrometry techniques, and other techniques. Among these techniques, X-ray photoelectron spectroscopy (XPS/ESCA) is the most preferable from a quantitative point of view. The relative quantitative value is determined by such technique in terms of atomic concentration (%), in general. Hereafter, the method of X-ray photoelectron spectroscopy employed in the present invention is described in detail.

According to the present invention, the "carbon content" of the hydrophilic thin membrane is defined as the "carbon content determined based on the analyzed C1s peak determined using an X-ray photoelectron spectroscopy apparatus." According to the present invention, the "percentage of carbon bound to oxygen" in the hydrophilic thin membrane is defined as the "percentage of carbon bound to oxygen determined based on the analyzed C1s peak determined using an X-ray photoelectron spectroscopy apparatus." Specifically, measurements can be carried out in the manner as described in JP Patent Publication (Kokai) No. 2007-312736 A.

(Pattern Configuration)

It is preferable that the substrate used for cell culture of the present invention comprise cell-adhesive regions and non-cell-adhesive regions positioned in a patterned manner. The pattern configuration can be any two-dimensional configuration without particular limitation, and it can be selected in accordance with, for example, cell type and tissue to be formed. For example, the pattern configuration can be line-shaped, tree-shaped (dendroid), netlike, lattice-shaped, circular, or square, and a circular or square figure in which the entire area constitutes a cell-adhesive region or non-cell-adhesive region can be formed.

Cell-adhesive regions and non-cell-adhesive regions are patterned in such a manner that a cell-adhesive region is positioned adjacent to a non-cell-adhesive region in the conductive region and a cell-adhesive region is positioned adjacent to a non-cell-adhesive region in the insulating region of the base material. Since a cell-adhesive region is positioned adjacent to a non-cell-adhesive region in a conductive region, cells are first allowed to adhere to the cell-adhesive region, culture is conducted in that state, and an electric potential is applied to the conductive region to modify the non-cell-adhesive region into the cell-adhesive region. Thus, cells can migrate to such modified region. Accordingly, patterning of regions to be modified into cell-adhesive regions can be determined in advance to regulate the region and the direction of cell migration in cell migration assays.

When a conductive region is patterned in a comb shape comprising a plurality of comb-tooth regions and a base supporting an individual comb-tooth region, for example, an elongated pattern so that a non-cell-adhesive region is positioned orthogonally to a comb-tooth region-that is, an elongated region across the conductive region and the insulating region, and preferably a line-shaped region-may be formed. Thus, cell migration assays can be carried out along the comb-tooth regions.

The width of an elongated region, and preferably a line-shaped region, orthogonal to the comb-tooth region needs to be smaller than the length of the comb-tooth region spreading from the base, so that cell culture can be carried out. The width of a line-shaped region is generally 1 μm to 2 cm, and preferably 50 μm to 1,000 μm. An elongated and preferably line-shaped region is patterned so that it is orthogonal to the comb-tooth region and is positioned at a distance from the comb-shaped base, and preferably at a distance as great as possible from the comb-shaped base. Thus, cells that had adhered to regions other than the elongated and preferably line-shaped region can migrate in the comb-tooth region modified into a cell-adhesive region after an electric potential is applied.

The substrate used for cell culture of the present invention can be prepared in the manner described above. According to an embodiment, the substrate can be prepared by a method comprising a step of providing a non-cell-adhesive hydrophilic membrane comprising an organic compound containing a carbon-oxygen bond across the entire surface of the base material comprising a conductive region and an insulating region provided thereon and a step of modifying a hydrophilic membrane to become cell adhesive by oxidation and/or degradation in a patterned manner so as to position a cell-adhesive region adjacent to a non-cell-adhesive region in a conductive region. It is occasionally preferable that a hydrophilic membrane be modified to become cell adhesive by oxidation and/or degradation in a patterned manner, so as to position a cell-adhesive region adjacent to a non-cell-adhesive region in an insulating region.

(Cells)

Floating cells, such as blood cells and lymphoid cells, or adhesive cells may be seeded on a substrate used for cell culture, and the present invention is preferably used for cells having adhesiveness. The present invention is also preferable for cells capable of migration. Examples of such cells include: cancer cells, such as hepatic cancer cells, glioma cells, colon cancer cells, renal cancer cells, pancreatic cancer cells, prostate cancer cells, bowel cancer cells, breast cancer cells, lung cancer cells, and ovarian cancer cells; hepatic cells that are the parenchymal cells of the liver; endothelial cells, such as Kupffer cells, vascular endothelial cells, and corneal endothelial cells; epidermal cells, such as fibroblasts, osteoblasts, osteoclasts, cells of the periodontal ligament, and epidermal keratinocytes; epidermal cells, such as tracheal epithelial cells, gastrointestinal epithelial cells, cervical epithelial cells, and corneal epithelial cells; mammary gland cells; pericytes; muscle cells, such as smooth muscle cells and cardiac muscle cells; renal cells; pancreatic islet cells; nerve cells, such as peripheral nerve cells and optic nerve cells; cartilage cells; and osteocytes. These cells may be primary cells directly sampled from tissue or organs or cells established from such primary cells by subculture over several generations. In addition, these cells may be undifferentiated embryonic stem cells, pluripotent stem cells, such as multipotent mesenchymal stem cells, unipotent stem cells, such as unipotent endothelial progenitor cells, or differentiated cells. A single type of cells may be cultured, or two or more types of cells may be cultured together.

A culture sample containing target cells is preferably subjected to dispersion treatment by which body tissue is finely ground and suspended in a liquid, separation treatment by which impurities such as cells other than the target cells and cell debris are removed from body tissue, or other forms of treatment, in advance.

Before seeding cells on a substrate used for cell culture, a culture sample containing target cells is preferably subjected to preliminary culture by various techniques in advance, so as to multiply the target cells. Preliminary culture can be carried out by conventional culture techniques, such as monolayer culture, culture in a coated dish, or culture on a gel. As a method of preliminary cell culture conducted by adhering cells to the surface of a support, the so-called monolayer culture technique is a means that is already known. Specifically, a culture sample and a culture solution are accommodated in a culture vessel, the culture vessel is maintained under given environmental conditions, and a given type of viable cells are selectively grown while adhering to the surface of a support such as a culture vessel. The apparatus, treatment conditions, and other factors are determined in accordance with, for example, a conventional monolayer culture technique. As a material for the surface of a support to which cells adhere and grow thereon, a material allowing efficient cell adhesion or growth, such as polylysine, polyethyleneimine, collagen, or gelatin, may be selected. The surface of a support, such as a glass petri dish, plastic petri dish, glass slide, glass cover, plastic sheet, or plastic film, may be coated with a chemical substance allowing efficient cell adhesion or growth (i.e., a cell adhesion factor).

After preliminary culture, the culture solution is removed from the culture vessel. Thus, unwanted components in the culture sample, such as clumped or fibrous impurities, that do not adhere to the surface of the support are removed, and viable cells adhered to the surface of the support can be selectively collected. Viable cells adhered to the surface of the support can be collected by, for example, EDTA-trypsin treatment.

The cells subjected to preliminary culture in the manner described above are seeded on a substrate used for cell culture in a culture solution. Methods and amounts of cells seeded are not particularly limited. For example, the method described in "*Soshiki Baiyo no Gijutsu* (Tissue Culture Technique)" (edited by the Japanese Tissue Culture Association, issued by Asakura Publishing Co., Ltd., 1999, pp. 266 to 270) can be employed. It is preferable that cells be seeded in an amount that would not require cell growth on a substrate used for cell culture and that cells adhere while forming a monolayer. In general, cells are preferably seeded so that $10^4$ to $10^6$ cells are contained per ml of the culture solution, and cells are preferably seeded so that $10^4$ to $10^6$ cells are contained per $cm^2$ of the substrate. Specifically, about $2 \times 10^5$ cells are seeded per 400 $mm^2$.

It is preferable that the substrate used for cell culture on which cells are seeded be cultured in a culture solution and the cells be allowed to adhere to the cell-adhesive region. As a culture solution, any cell culture medium that is generally used in the art can be used without particular limitation. For example, basal media described in "*Soshiki Baiyo no Gijutsu* (Tissue Culture Technique)," (vol. 3, edited by the Japanese Tissue Culture Association, issued by Asakura Publishing Co., Ltd., p. 581), such as MEM medium, BME medium, DME medium, aMEM medium, IMDM medium, ES medium, DM-160 medium, Fisher medium, F12 medium, WE medium, and RPMI 1640 medium, can be used in accordance with types of cells to be used. Blood serum (fetal bovine serum or the like), various growth factors, antibiotics, amino acids, and other substances may further be added to basal media. Alternatively, commercially available serum-free media, such as Gibco serum-free medium (Invitrogen), can be used, for example.

The duration of cell culture varies depending on, for example, the necessity for cell manipulation at the time of culture. It is generally 6 to 96 hours, and preferably 12 to 72 hours. Culture is generally conducted at 37° C. Culture is preferably conducted in the presence of about 5% $CO_2$ with the use of a $CO_2$ cell culture incubator. After culture, the substrate used for cell culture is washed, cells that did not adhere thereto are washed away, and cells are allowed to adhere selectively to the cell-adhesive region.

(Cell Migration Assays)

As described above, cells are seeded on the substrate used for cell culture of the present invention, cell culture is conducted, cells are allowed to adhere to the cell-adhesive region, an electric potential is applied to the conductive region so as to modify the non-cell-adhesive region in the conductive region into a cell-adhesive region, and cell migration occurring thereafter is observed. Thus, cell migration can be assayed.

In other words, the method for cell migration assays of the present invention comprises:

(i) a step of seeding cells on the substrate used for cell culture of the present invention to allow the cells to adhere to the cell-adhesive region;

(ii) a step of applying an electric potential to the conductive region so as to modify a non-cell-adhesive region in the conductive region into a cell-adhesive region; and (iii) a step of observing the cells adhered to the cell-adhesive region in the conductive region that migrate to the region modified to become cell adhesive in step (ii).

In step (i), it is preferable that cells be seeded, cell culture be conducted, and cells be allowed to adhere to the cell-adhesive region. It is further preferable that the substrate used for cell culture be washed so as to wash away the cells that did not adhere to the substrate, and that cells be allowed to adhere selectively to the cell-adhesive region.

In step (ii), an electric potential applied to the conductive region is preferably a positive electric potential. Thus, the non-cell-adhesive region can be effectively modified into a cell-adhesive region. When a conductive region is composed of an ITO membrane, in particular, blackening can be prevented, and cell migration can be satisfactorily observed.

A person skilled in the art can adequately determine an electric potential to be applied. It is generally 1 to 10 V, and preferably 2 to 5 V. The duration during which an electric potential is applied is generally 0.5 to 60 minutes, and preferably 1 to 10 minutes.

An adequate electric potential varies depending on a type of solvent that is in contact with an electrode, an electrode material, an electrode configuration, and other factors. In general, an electric potential to be applied is adequately determined so that a non-cell-adhesive region is modified into a cell-adhesive region and cells are not adversely affected.

An electric potential may be applied between conductive regions on a flat base material (e.g., between one ITO and another ITO). Alternatively, a counter electrode of Pt or another substance may be provided on a flat base material, and an electric potential may be applied between a conductive region and the counter electrode (e.g., between an ITO and Pt). For the purpose of accurate regulation of an electric potential, a reference electrode, such as Ag/AgCl, may be provided on a flat base material. It is not necessary to provide such counter electrode or reference electrode on a flat base material (an electrode may be soaked in a culture solution).

Observation of cell migration involves measurements of cell migration speed, migration direction, cellular configuration at the time of migration, connection between adjacent cells, and other factors. Measurements of cell migration speed can be carried out by measuring the area and the distance of a cell infiltrating a pattern such as a line-shaped pattern of a comb-tooth region.

If a comb-tooth region of a line-shaped pattern of the substrate used for cell culture of the present invention is narrow, the area of a cell-adhesive region in the conductive region in the vicinity of the non-cell-adhesive region in the conductive region is reduced, and the number of cells that can be involved in migration is disadvantageously decreased. When a cell-adhesive region is positioned adjacent to a non-cell-adhesive region in the insulating region, however, cells adhered to the cell-adhesive region in the insulating region in the vicinity of the non-cell-adhesive region of the conductive region can migrate. As a result, the total number of cells that can migrate is increased, and migration can be effectively evaluated.

Hereafter, embodiments of the substrate used for cell culture and the method for cell migration assays of the present invention are described with reference to the drawings.

An embodiment of the method for producing the substrate used for cell culture of the present invention is shown in FIGS. 1(1) to (3). As shown in FIG. 1(1), at the outset, a conductive region (b) and an insulating region (a) are provided on a base material in such a manner that the conductive region is patterned into a comb shape comprising a plurality of comb-tooth regions (c) and a base (d) each supporting an individual comb-tooth region.

Subsequently, a non-cell-adhesive hydrophilic membrane comprising an organic compound containing a carbon-oxygen bond is provided across the entire surface of the base material, as shown in FIG. 1(2). Thereafter, the hydrophilic membrane is subjected to oxidation and/or degradation in a patterned manner (i.e., a non-cell-adhesive region is an elongated (line-shaped) region positioned orthogonally to the comb-tooth region) in order to modify the membrane to become cell adhesive, as shown in FIG. 1(3). Thus, a substrate used for cell culture comprising a conductive region in which a cell-adhesive region (b) is positioned adjacent to a non-cell-adhesive region (b') and an insulating region in which a cell-adhesive region (a) is positioned adjacent to a non-cell-adhesive region (a') can be obtained. An embodiment of the method for cell migration assays of the present invention is shown in FIG. 1(3') to (5'). As shown in FIG. 1(3'), at the outset, cells are seeded on a substrate used for cell culture to allow cells (e) to adhere to the cell-adhesive region. Subsequently, an electric potential, and preferably a positive electric potential, is applied to the conductive region (A), so as to modify the non-cell-adhesive region (b') in the conductive region into the cell-adhesive region (b) (4'). Thereafter, migration of cells adhered to the cell-adhesive region in the conductive region to a region modified to become cell adhesive is observed (5').

(Other Embodiments)

Other preferable embodiments of the substrate used for cell culture of the present invention are described with reference to FIG. 3 to FIG. 7. Various conditions of this embodiment, such as materials and methods for producing a substrate used for cell culture, the configuration of the substrate used for cell culture, cell culture methods, cell culture conditions and reagents to be used therefor, cells to be cultured, the electric potential to be applied, and the method of application of an electric potential, are the same as those described in other embodiments of the present invention, unless otherwise specified herein.

Figure 3:
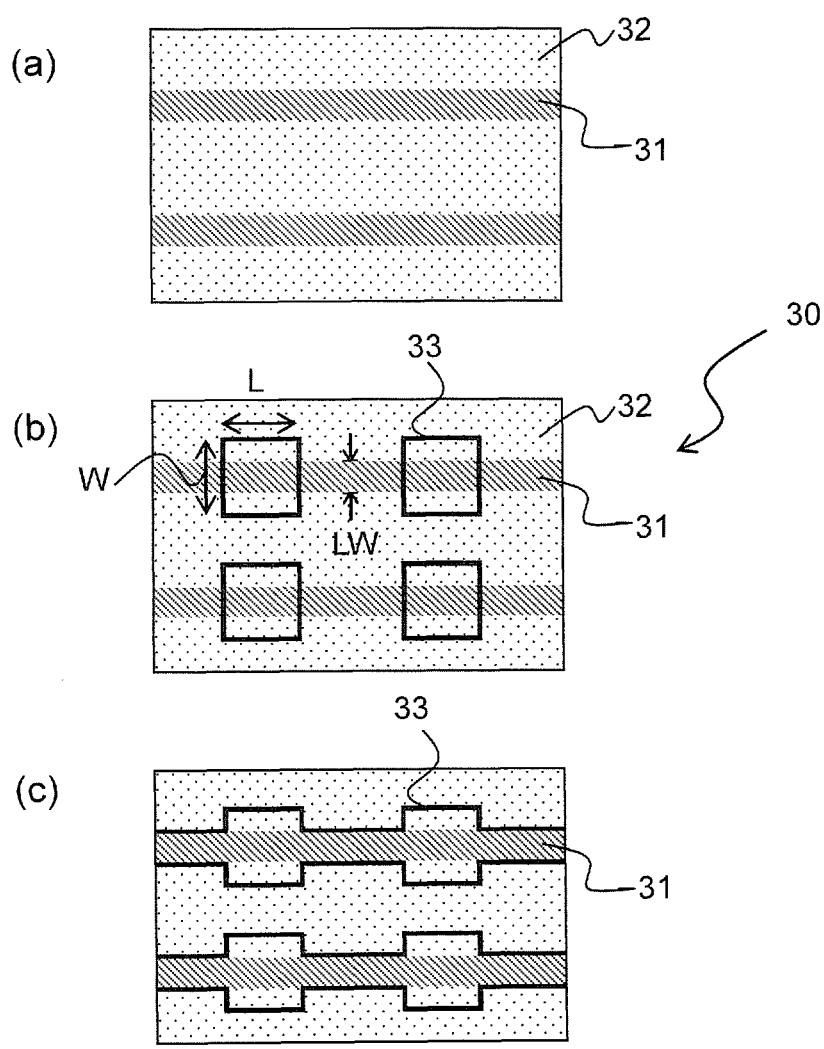
FIG. 3 shows an embodiment of the substrate used for cell culture of the present invention.

As shown in FIG. 3(b), the substrate 30 used for cell culture according to this embodiment comprises at least 1 line-shaped conductive region 31 thereon and insulating regions 32 provided on both sides along the longitudinal direction of the line-shaped conductive region 31. The line-shaped conductive region 31 comprises one or more cell-adhesive region(s) 33 entirely or partially composed of the line-shaped conductive region(s) provided at one position or at two or more positions different along the longitudinal direction. In FIGS. 3 to 7, a thick frame indicates an outer periphery of the cell-adhesive region, and a region outside the frame indicates a non-cell-adhesive region. When a plurality of cell-adhesive regions are present, such regions are positioned at a distance from each other. As shown in FIGS. 3 to 6, when regions in the line-shaped conductive regions 31, 50, and 60 constitute part of the cell-adhesive regions 33, and 62, other regions in the cell-adhesive regions 33, and 62 are constituted by the insulating regions 32, 55, and 61 located adjacent to the conductive regions. As described below with reference to FIG. 7, the entire cell-adhesive region 73 may constitute a line-shaped conductive region at a certain position (i.e., a broad area 71). In such a case, the line-shaped conductive region has a width in accordance with the width of the cell-adhesive region at a position corresponding to the cell-adhesive region in the longitudinal direction. Among the line-shaped conductive region 31 and the insulating region 32, a region outside the cell-adhesive region 33 (i.e., a region that is not surrounded by a frame) is a non-cell-adhesive region. The dimension in the longitudinal direction of the line-shaped conductive region 31 located adjacent to the cell-adhesive region 33 is defined as the length of the cell-adhesive region (L), the dimension in the direction orthogonal thereto in the longitudinal direction of a cell-adhesive region 33 on a flat base material is defined as the width of the cell-adhesive region (W), and the length (L) and the width (W) of each cell-adhesive region are 1 μm to 500 μm. The line width of a region outside the cell-adhesive region of the line-shaped conductive region 31 (LW, a dimension in a direction orthogonal to the region in the longitudinal direction on a flat base material) is 0.1 μm to 10 μm, and the line width (LW) is smaller than the width (W) of the cell-adhesive region 33 connected thereto. A non-cell-adhesive region of the line-shaped conductive region 31 (a region outside the cell-adhesive region 33 of the line-shaped conductive region 31 shown in FIG. 3(b)) can be preferably modified to become cell adhesive with the application of an electric potential. When an electric potential is applied, specifically, the line-shaped conductive region 33 previously provided is integrated with the entire line-shaped conductive region 31, and a line-shaped cell-adhesive region having a broad area corresponding to the cell-adhesive region 33 previously provided is provided at a plurality of positions different along the longitudinal direction, as shown in FIG. 3(c).

According to this embodiment of the present invention, the cell-adhesive region 33 preferably has dimensions, a configuration, and an area that allow selective adhesion of 1 to several cells-for example, 1 to 3 cells, preferably 1 or 2 cells, and particularly preferably 1 cell-to be cultured. To this end, the dimensions, the configuration, and the area of the cell-adhesive region 33 can be adequately determined in accordance with types of cells to be cultured. The length (L) and the width (W) of the cell-adhesive region 33 as defined above are each generally 1 μm to 500 μm, preferably 10 μm to 200 μm, and more preferably 25 μm to 50 μm. The proportion of the length to the width of a cell-adhesive region are not particularly limited. When the length of a cell-adhesive region is designated as 1, the width of the cell-adhesive region is generally 0.5 to 2, preferably 0.7 to 1.5, more preferably 0.8 to 1.3, particularly preferably 0.95 to 1.05, and most preferably 1. While a square is exemplified as a configuration of the cell-adhesive region in FIGS. 3 to 7, the configuration is not limited thereto. For example, the cell-adhesive region may be a tetragon, such as a square, rectangle, rhombus, or parallelogram, a polygon with three, five, six, or more sides, or a circle, such as a true circle, an ellipse or an oval. When the length and the width of the cell-adhesive region are each 1 µm to 500 µm, the area of the tetragonal cell-adhesive region would be 1 µm² to 250,000 µm², and that of the circular cell-adhesive region would be about 0.8 µm² to 196,350 µm². The area of the cell-adhesive region is preferably 50 µm² to 40,000 µm², and more preferably 625 µm² to 2,500 µm² (490 µm² to 1,963 µm² if the cell-adhesive region is circular).

The line width (LW) of the line-shaped conductive region is preferably 0.1 µm to 20 µm, more preferably 0.1 µm to 10 µm, and particularly preferably 1 µm to 5 µm. When the line width (LW) is within such range, the line-shaped conductive region would have a width that allows the cells adhered to the cell-adhesive region to spread but does not allow the cells to migrate. Specifically, the width can be adequately determined in accordance with types of cells to be cultured. In order to allow the cells adhered to the cell-adhesive region to spread while preventing such cells from migrating, the line width (LW) of the line-shaped conductive region is made smaller than the width (W) of the cell-adhesive region 33 previously formed. When the width (W) of the cell-adhesive region is designated as 1, for example, the line width (LW) of the line-shaped conductive region connected to the cell-adhesive region can be preferably 0.2 or less, and more preferably 0.01 to 0.2.

The configuration of the line-shaped conductive region may be straight or curved. In addition, a plurality of line-shaped conductive regions may be combined to form an arbitrary configuration, such as a dendroid, netlike, or lattice configuration, as described below.

According to an embodiment in which cell-adhesive regions are provided at two or more positions different along the longitudinal direction of the line-shaped conductive region, the length of a region that connects two cell-adhesive regions in the line-shaped conductive region can be adequately determined in accordance with types of cells to be cultured. It is generally 10 µm to 10 mm, and preferably 50 µm to 200 µm. When the substrate is used for culture of nerve cells, the length may be 100 mm to 30 cm from the viewpoint of the high stretching ability of the axis cylinder.

The substrate used for cell culture according to this embodiment of the present invention comprises, on its surface, a line-shaped conductive region 31 and an insulating region 32, as shown in FIG. 3(a). A hydrophilic membrane or the like is provided across the entire surface of the base material comprising such regions provided thereon, so as to prepare a non-cell-adhesive substrate. Subsequently, the hydrophilic membrane is subjected to oxidation and/or degradation in a patterned manner, so as to provide 1 or a plurality of cell-adhesive regions 33, as shown in FIG. 3(b).

Figure 4:
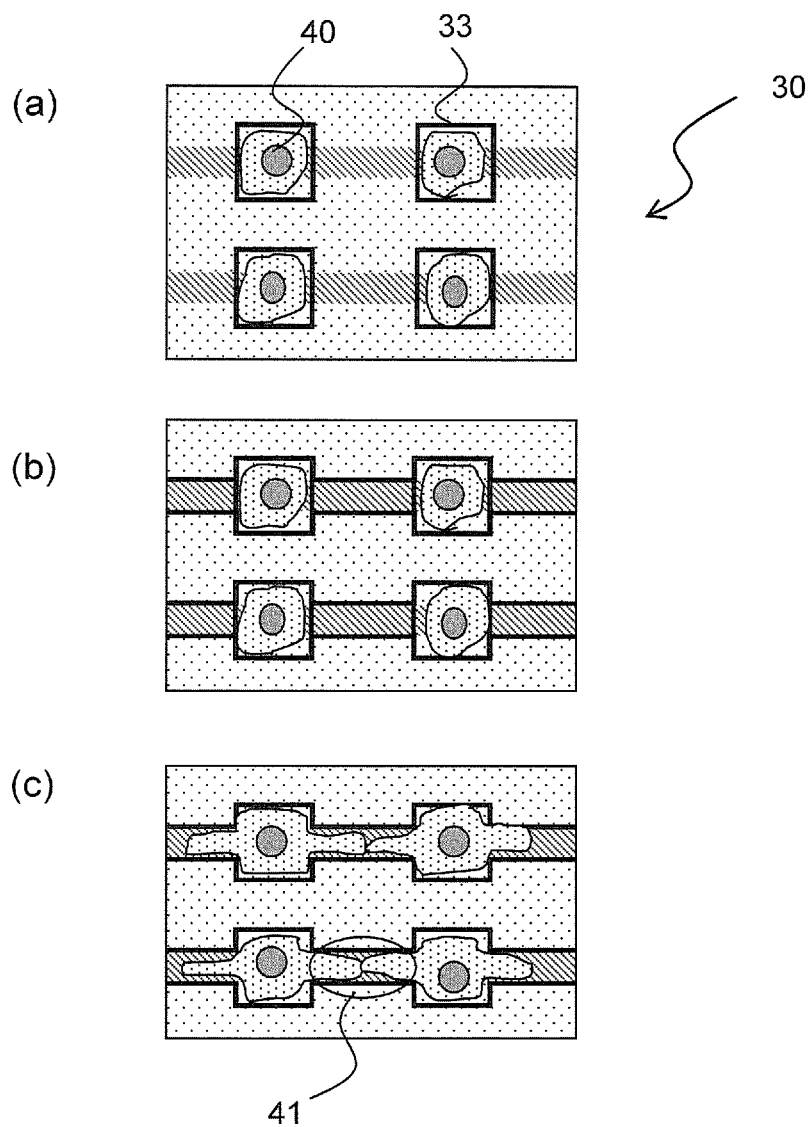
FIG. 4 shows a process of morphologically changing some cells using the substrate used for cell culture shown in FIG. 3.

A method for using the substrate 30 used for cell culture according to this embodiment of the present invention is described with reference to FIG. 4. At the outset, cells 40 are seeded on the substrate 30 used for cell culture of the present invention to allow the cells to adhere to the cell-adhesive region 33 (FIG. 4(a)). In this case, 1 to several-for example, 1 to 3, preferably 1 or 2, and particularly preferably 1-of the cells 40 selectively adhere to each of the cell-adhesive regions 33. Subsequently, an electric potential is applied to the line-shaped conductive region to modify the non-cell-adhesive region in the line-shaped conductive region into a cell-adhesive region, as shown in FIG. 4(b). With the elapse of time, the configuration of some of the cells 40 adhered to the cell-adhesive region 33 is altered and such cells spread along the line-shaped conductive region 31, which is modified to become cell adhesive, as shown in FIG. 4 (c). Through observation of the cells, cellular functions and the like can be examined. Cells can be observed from various points of view. For example, the speed of configurational changes, the distance, and the cellular configuration after configurational changes can be observed. With the use of the substrate of the present invention comprising cell-adhesive regions provided at two or more positions different along the longitudinal direction of the line-shaped conductive region, cellular interactions with other cells connected through the line-shaped conductive region or other phenomena can also be observed. Based on this method, cell-cell interactions can be evaluated.

The method can also be used for construction of a circuit-like cellular construct. As shown in FIG. 4(c), the substrate of the present invention comprising cell-adhesive regions provided at two or more positions different along the longitudinal direction of the line-shaped conductive region is used to culture the cells 40 while an electric potential is applied. This causes configurational changes in some of the cells 40 adhered to the cell-adhesive region 33, the cells spread along the line-shaped conductive region, which is modified to become cell adhesive, and a connection 41 is generated between the cells 40 and other cells connected through the line-shaped conductive region. This method can be applied to any cells without particular limitation. For example, nerve cells can be used as culture cells, and stretching of the axis cylinder along the line-shaped conductive region, which is modified to become cell adhesive, is induced. Thus, a neural network having a desirable configuration can be formed.

When a thin line-shaped cell-adhesive region is newly formed, following seeding of cells, as in the case of the present invention, the risk of cells adhering to a line-shaped region at the time of cell seeding can be reduced, compared with a case in which cells are seeded on a substrate comprising a line-shaped cell-adhesive region provided in advance.

Figure 5:
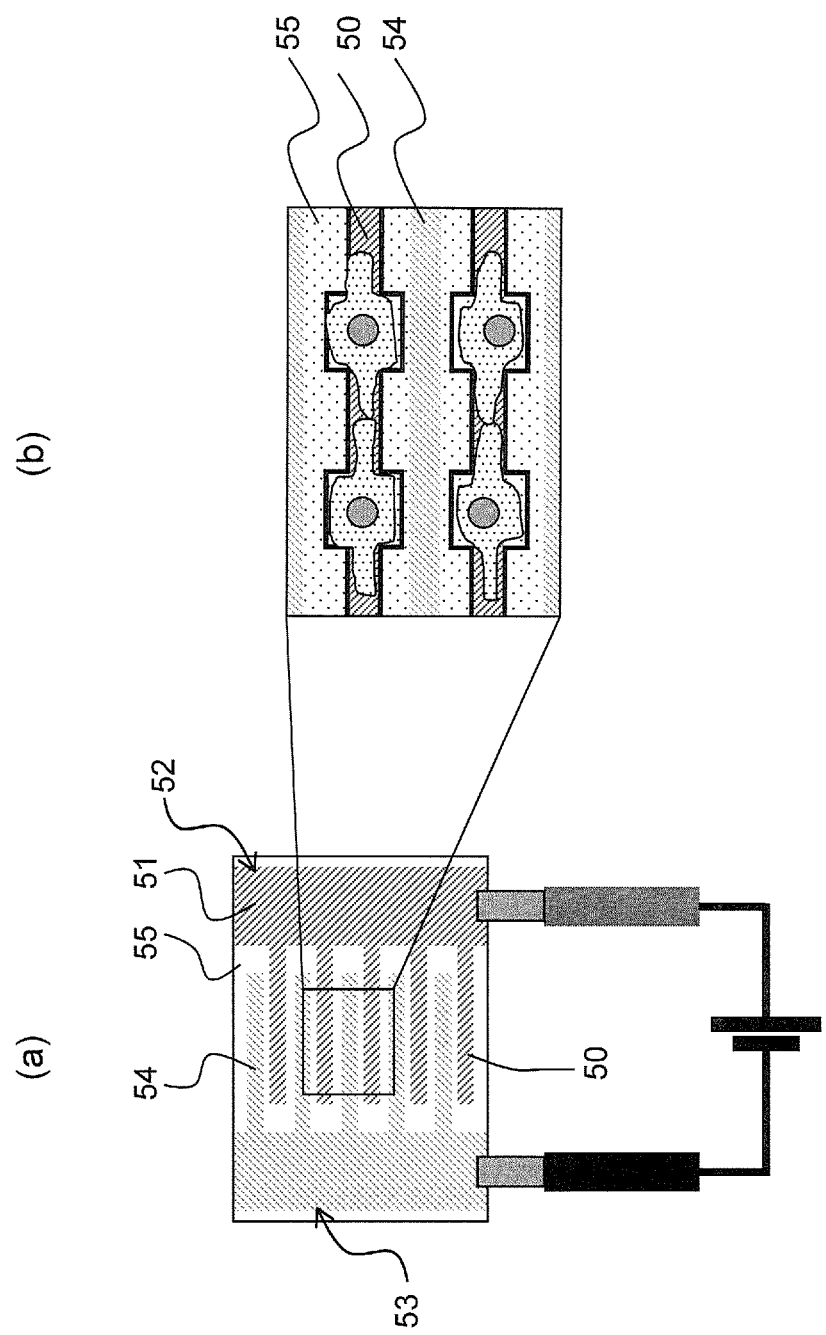
FIG. 5 shows a more specific configuration of the substrate used for cell culture shown in FIG. 3.

The configuration of the entire conductive region is not particularly limited, and it can be patterned in, for example, a comb shape 52 comprising a plurality of comb-tooth regions 50 and a base 51 each supporting an individual comb-tooth region 50, as shown in FIG. 5. In such a case, each comb-tooth region 50 can serve as a line-shaped conductive region. As a counter electrode, a comb-shaped conductive region 53 having the same configuration and comprising a plurality of comb-tooth regions 54 is provided, and comb-tooth regions 50 and comb-tooth regions 54 can be positioned so as to be alternately engaged with each other. FIG. 5(a) shows an overall view of the apparatus, and FIG. 5(b) shows an enlarged view of the part in the frame indicated in FIG. 5(a).

Figure 6:
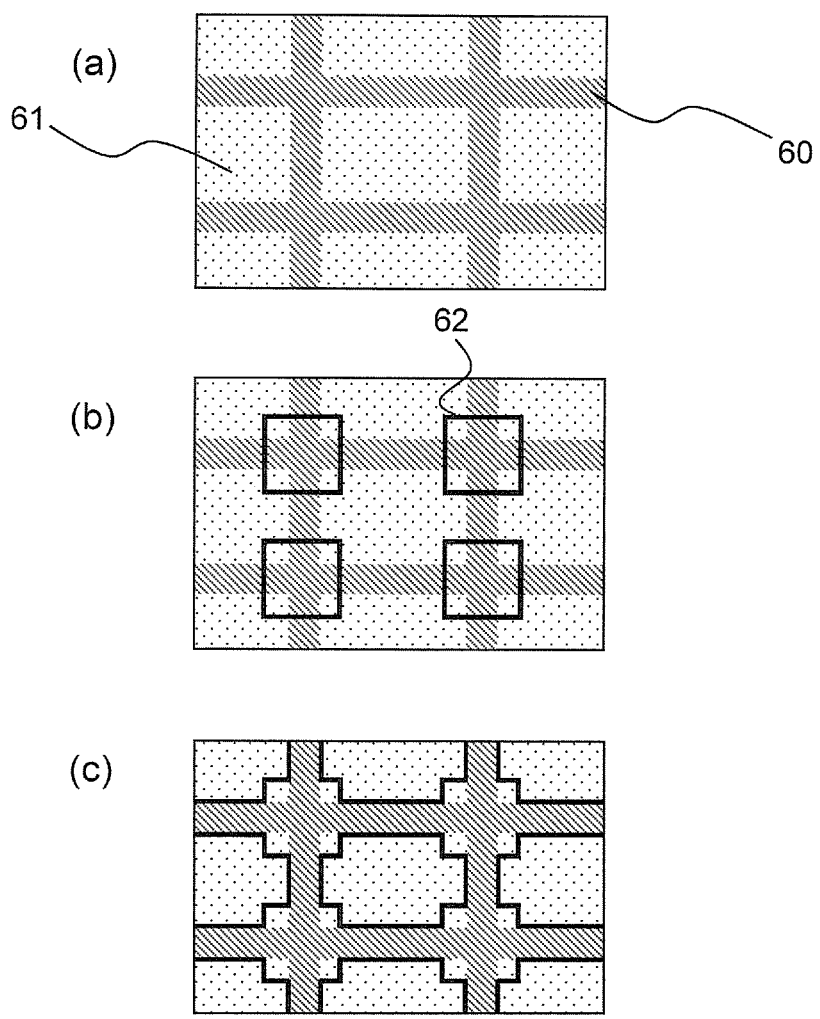
FIG. 6 shows an embodiment of the substrate used for cell culture of the present invention.
Figure 7:
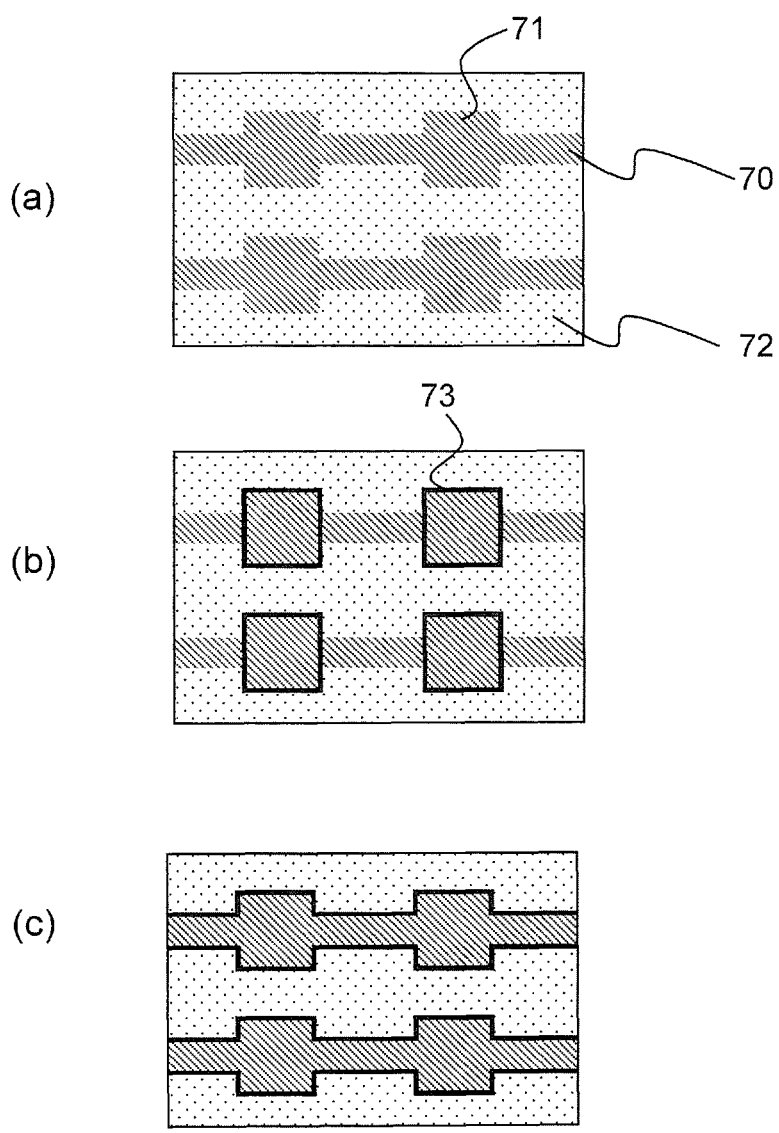
FIG. 7 shows an embodiment of the substrate used for cell culture of the present invention.

The number and the positions of the line-shaped conductive regions are not particularly limited. For example, a plurality of line-shaped conductive regions 60 may be positioned in a lattice form, as shown in FIG. 6. In such a case, a cell-adhesive region 62 can be provided so as to include intersection points of the lattice. According to this embodiment, a line-shaped conductive region 60 can be modified to become cell adhesive with application of an electric potential (FIG. 6(c)).

FIG. 3 to FIG. 6 show embodiments in which a cell-adhesive region is provided so as to include part of the line-shaped conductive region and part of the insulating region adjacent thereto. However, the entire cell-adhesive region may be a conductive region. As shown in FIG. 7(a), for example, a line-shaped conductive region 70 comprising a plurality of broad areas 71 at positions different along the longitudinal direction is provided. A cell-adhesive region 73 may be provided to overlap with the broad area 71 (FIG. 7(b)), an electric potential may be applied thereto, and the line-shaped conductive region 70 can be thus modified to become cell adhesive (FIG. 7(c)).

Hereafter, the present invention is described with reference to the examples, although the present invention is not limited to the examples.

EXAMPLES

1. Production of Electrode Base Material

An indium tin oxide (ITO) membrane was provided on a 10 cm×10 cm square alkali-free glass to a thickness of 150 nm by sputtering, and the resulting membrane was subjected to resist coating, exposure using a photomask, development, and etching to prepare a comb-shaped ITO electrode base material with a line width of 100 μm (FIG. 1(1)).

2. Production of Substrate Used for Cell Culture (First-Phase Reaction)

While agitating a mixture of 39.0 g of toluene and 750 μl of epoxysilane TSL8350 (GE Toshiba Silicones Co., Ltd.), a catalytic amount of triethylamine was added thereto, and the mixture was further agitated at room temperature for several minutes. The ITO base material neuron network washed with UV application was soaked in the epoxysilane solution, followed by agitation at room temperature for 19 hours. Thereafter, the ITO base material provided with an undercoat was washed with ethanol, rinsed, and then dried.

(Second-Phase Reaction)

A catalytic amount of concentrated sulfuric acid was slowly added to 15 g of tetraethylene glycol during agitation, and the mixture was further agitated at room temperature for several minutes. The base material treated with epoxysilane was soaked in the tetraethylene glycol described above, and a reaction was allowed to proceed at 80° C. for 60 minutes. After the reaction, the base material was thoroughly rinsed and then dried. Thus, a substrate comprising a hydrophilic thin membrane provided thereon was obtained (FIG. 1(2)).

(Oxidation)

A photomask coated, on its entire surface, with a titanium oxide-based photocatalyst was prepared. The photomask had a 250-μm-square aperture pattern at intervals of 500 μm, and it was 5 inches in length provided with an aperture with a width of about 1.5 cm on its periphery. The illumination of the exposure apparatus was measured at the wavelength of 360 nm in advance, and the measured value was employed as an indication for determining the duration of exposure. The illumination was 25 mW/cm$^2$. The ITO substrate comprising a hydrophilic thin membrane provided thereon and the quarts plate provided with a catalyst were positioned in such a manner that a hydrophilic thin membrane was opposed to a photocatalyst layer of the photomask and that the comb-tooth region in the comb-shaped conductive region of the ITO substrate was orthogonal to the squared pattern of the photomask. The photomask was positioned inside the exposure apparatus, so that the substrate would be irradiated with light from the back of the photomask. The resultant was exposed to light for 120 seconds for oxidation and then cut into 25 mm×25 mm square pieces for convenience of culture (FIG. 1(3)).

3. Cell Culture

The substrate cut in the manner described above was sterilized with ethylene oxide gas. Sterilized cloning rings (Φ 8 mm) were embedded in the substrate, and mouse fibroblasts (5×10$^4$ cells) were seeded therein. Culture was conducted using DMEM medium containing 10% serum in an incubator at 37° C. in the presence of 5% $CO_2$ for 24 hours. As a result of observation under a phase-contrast microscope, cells were found to adhere selectively to the oxidated regions in the confluent state (FIG. 1(3')).

4. Application of Electric Potential

Figure 2:
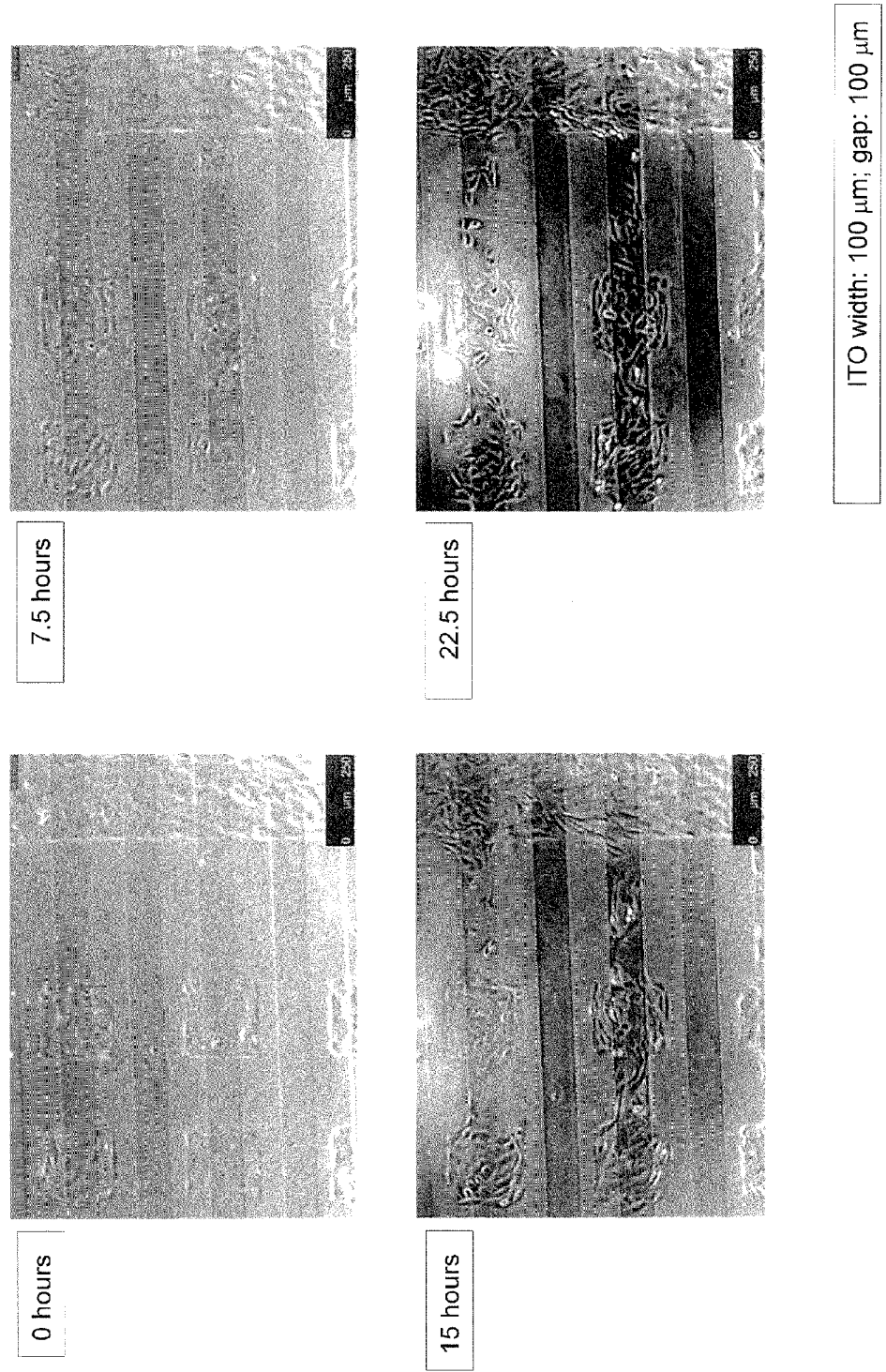
FIG. 2 shows the results of the application of an electric potential test (2 V, 1 minute) with photographs showing the results of cell migration assays conducted in the examples.

The comb-shaped ITO substrate was connected to a circuit and an electric potential of +2V was applied for 2 minutes. With the elapse of time, the cells that had adhered in accordance with the square pattern of the photomask were observed to migrate while deforming the pattern selectively on the electrode to which a positive electric potential had been applied. Such cells were observed to have migrated about 100 μm on a 100-μm-wide electrode 7.5 hours later (FIG. 1(4'), (5'), FIG. 2).

Description Of Numeral References

30: Substrate used for cell culture
31: Conductive region
32: Insulating region
33: Cell-adhesive region
40: Cell
41: Cell-cell connection
50: Comb-tooth region (line-shaped conductive region)
51: Base
52: Comb-shaped electrode
53: Comb-shaped electrode
54: Comb-tooth region as counter electrode
55: Insulating region
60: Conductive region
61: Insulating region
62: Cell-adhesive region
70: Conductive region
71: Broad area in conductive region
72: Insulating region
73: Cell-adhesive region All publications, patents, and patent applications cited herein are incorporated herein by reference in their entirety.

The invention claimed is:

1. A cell culture substrate, comprising a base material comprising a conductive region and an insulating region provided thereon, cell-adhesive regions and non-cell-adhesive regions provided in the conductive region, and non-cell-adhesive regions provided in the insulating region,
   wherein one of the cell-adhesive regions is positioned adjacent to one of the non-cell-adhesive regions in the conductive region,
   the conductive region comprises a line-shaped conductive region,
   the insulating region is disposed on both sides of the line-shaped conductive region along a longitudinal direction of the line-shaped conductive region,
   the line-shaped conductive region comprises one or more of the cell-adhesive regions, wherein the one or more of the cell-adhesive regions are entirely or partially composed of the line-shaped conductive region(s) and are provided at one position or at two or more positions different along the longitudinal direction,
   when the line-shaped conductive region is a part of the one or more of the cell-adhesive regions, the one or more of the cell-adhesive regions further include the insulating region adjacent to the line-shaped conductive region, and the line-shaped conductive region and the insulating region outside the one or more of the cell-adhesive regions are the non-cell-adhesive regions, and when a dimension of one of the cell-adhesive regions in the longitudinal direction of the line-shaped conductive region is defined as a length of the one of the cell-adhesive regions and a dimension of the one of the cell-adhesive regions in a direction orthogonal to the longitudinal direction is defined as a width of the one of the cell-adhesive regions, the length and the width of the one of the cell-adhesive regions are 1 μm to 500 μm, and a line width of the line-shaped conductive region outside the one of the cell-adhesive regions is 0.1 μm to 10 μm, and the line width is smaller than the width of the one of the cell-adhesive regions adjacent thereto.

2. The cell culture substrate according to claim 1, wherein the insulating region further comprises cell-adhesive regions, and one of the cell-adhesive regions in the insulating region is positioned adjacent to one of the non-cell-adhesive regions in the insulating region.

3. The cell culture substrate according to claim 1, wherein the non-cell-adhesive regions in the conductive region can be modified to become cell adhesive by applying an electric potential to the conductive region.

4. The cell culture substrate according to claim 1, wherein the cell-adhesive regions are modified from a non-cell-adhesive hydrophilic membrane comprising an organic compound containing a carbon-oxygen bond by oxidation and/or degradation and the non- cell-adhesive regions are composed of a hydrophilic membrane comprising an organic compound containing a carbon-oxygen bond.

5. The cell culture substrate according to claim 4, wherein the organic compound containing a carbon-oxygen bond is an alkylene glycol oligomer.

6. The cell culture substrate according to claim 1, wherein the conductive region is patterned in a comb shape comprising a plurality of comb-tooth regions and a base supporting an individual comb-tooth region.

7. The cell culture substrate according to claim 6, wherein the non-cell-adhesive region is patterned in an elongated region that is positioned to be orthogonal to the comb-tooth region.

8. The cell culture substrate according to claim 6, wherein the width of the comb-tooth region in the conductive region is 0.1 μm to 500 μm.

9. The cell culture substrate according to claim 6, wherein the intervals between the comb-tooth regions in the conductive region are between 10 μm and 1,000 μm.

10. The cell culture substrate according to claim 1, wherein the conductive region comprises an indium tin oxide membrane on the surface of the base material.

* * * * *